United States Patent

Spivack et al.

(10) Patent No.: US 6,355,597 B1
(45) Date of Patent: Mar. 12, 2002

(54) CATALYST SYSTEM FOR PRODUCING AROMATIC CARBONATES

(75) Inventors: James Lawrence Spivack, Cobleskill; Donald Wayne Whisenhunt, Jr., Schenectady, both of NY (US); James Norman Cawse, Pittsfield, MA (US); Bruce Fletcher Johnson, Scotia; Kirill Shalyaev, Clifton Park, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/559,855

(22) Filed: Apr. 27, 2000

Related U.S. Application Data

(62) Division of application No. 09/301,702, filed on Apr. 29, 1999, now Pat. No. 6,114,563.

(51) Int. Cl.[7] .......................... B01J 23/16; B01J 23/32; B01J 23/72; B01J 27/128; B01J 27/130
(52) U.S. Cl. .................... 502/353; 502/304; 502/324; 502/331; 502/333; 502/345; 502/350; 502/229; 502/230
(58) Field of Search ................. 502/302, 304, 502/324, 333, 331, 345, 350, 353, 229, 230; 558/270–274

(56) References Cited

U.S. PATENT DOCUMENTS

| | | | |
|---|---|---|---|
| 4,187,242 A | * | 2/1980 | Chalk .......................... 260/463 |
| 5,231,210 A | | 7/1993 | Joyce et al. |
| 5,239,106 A | | 8/1993 | Shafer |
| 5,284,964 A | | 2/1994 | Pressman et al. |
| 5,373,083 A | | 12/1994 | King, Jr. et al. |
| 5,380,907 A | | 1/1995 | Mizukami et al. |
| 5,399,734 A | | 3/1995 | King, Jr. et al. |
| 5,498,789 A | | 3/1996 | Takagi et al. |
| 5,543,547 A | | 8/1996 | Iwane et al. |
| 5,726,340 A | | 3/1998 | Takagi et al. |
| 5,760,272 A | * | 6/1998 | Pressman et al. ............ 558/274 |
| 5,856,554 A | * | 1/1999 | Buysch et al. .............. 558/274 |
| 6,114,563 A | * | 9/2000 | Spivack et al. ............. 558/274 |
| 6,143,913 A | * | 11/2000 | Spivack et al. ............. 558/274 |
| 6,197,991 B1 | * | 3/2001 | Spivack et al. ............. 558/274 |
| 6,201,146 B1 | * | 3/2001 | Spivack et al. ............. 558/274 |

FOREIGN PATENT DOCUMENTS

| | | |
|---|---|---|
| DE | 736325 | 3/1996 |
| EP | 0503091 | * 9/1992 |
| EP | 0507546 | * 10/1992 |
| EP | 0 581 240 | 2/1994 |
| EP | 0736324 | * 10/1996 |
| EP | 0801051 | * 10/1997 |
| JP | 10158221 | 6/1980 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-278715 | 10/1997 |
| JP | 97-278716 | 10/1997 |

\* cited by examiner

Primary Examiner—Mark L. Bell
Assistant Examiner—Patricia L. Hailey
(74) Attorney, Agent, or Firm—Ben P. Patel; Noreen C. Johnson

(57) ABSTRACT

A catalyst system for economically producing aromatic carbonates from aromatic hydroxy compounds. In one embodiment, the present invention provides a carbonylation catalyst system that includes a catalytic amount of an inorganic co-catalyst containing bismuth. In various alternative embodiments, the carbonylation catalyst system can include an effective amount of a palladium source and an effective amount of a halide composition. Further alternative embodiments can include catalytic amounts of various inorganic co-catalyst combinations.

27 Claims, 1 Drawing Sheet

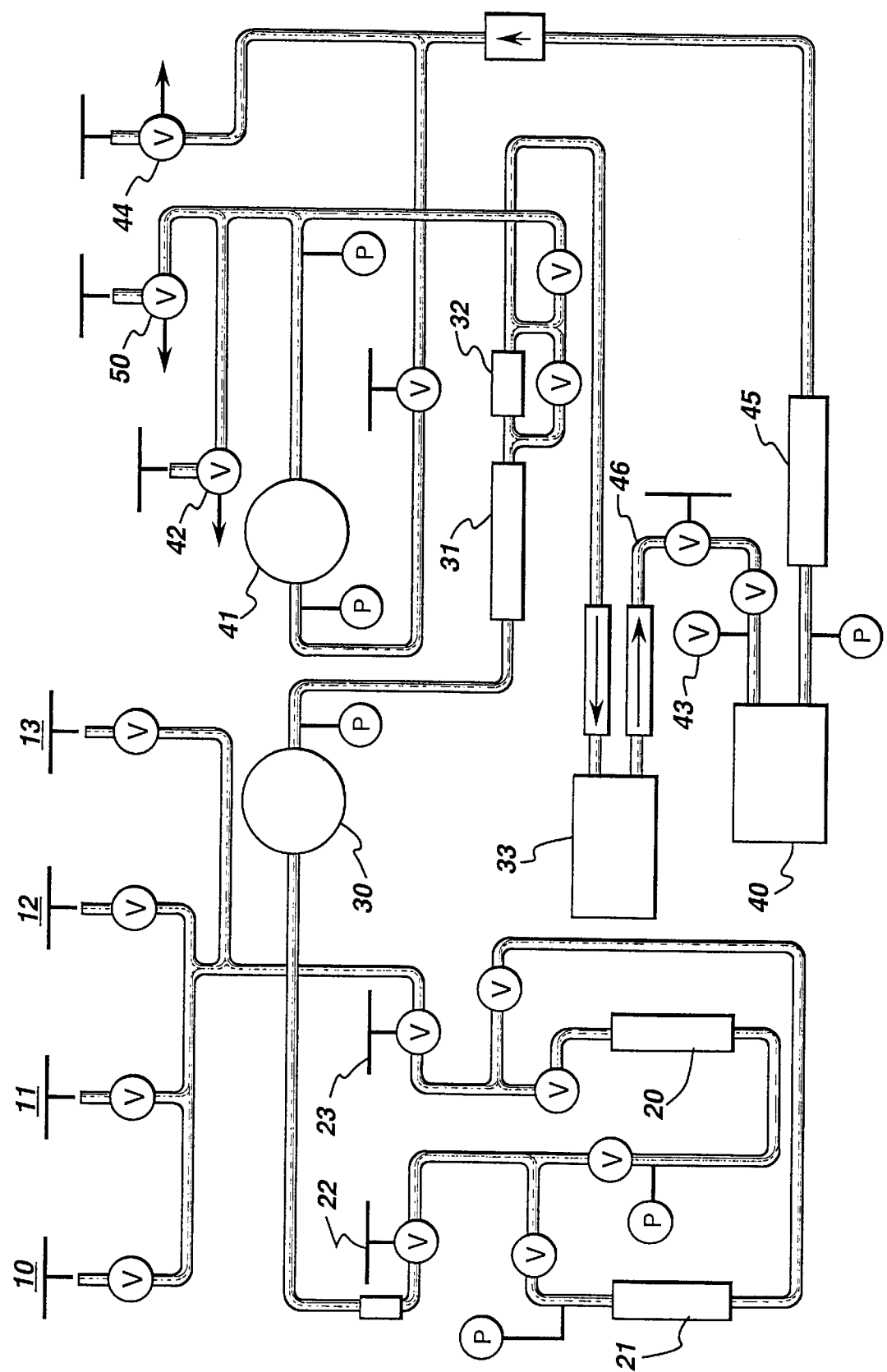

CATALYST SYSTEM FOR PRODUCING AROMATIC CARBONATES

CROSS REFERENCE TO RELATED APPLICATIONS

This application is a division of application Ser. No. 09/301,702, filed Apr. 29, 1999, now U.S. Pat. No. 6,114,563, entitled "METHOD AND CATALYST SYSTEM FOR PRODUCING AROMATIC CARBONATES" and, accordingly, claims priority to and the benefit of the filing date of said application under 35 U.S.C. §120. The parent application is incorporated herein by reference.

BACKGROUND OF THE INVENTION

1. Field of the Invention

The present invention is directed to a catalyst system for producing aromatic carbonates and, more specifically, to a catalyst system for producing diaryl carbonates through the carbonylation of aromatic hydroxy compounds.

2. Discussion of Related Art

Aromatic carbonates find utility, inter alia, as intermediates in the preparation of polycarbonates. For example, a popular method of polycarbonate preparation is the melt transesterification of aromatic carbonates with bisphenols. This method has been shown to be environmentally superior to previously used methods which employed phosgene, a toxic gas, as a reagent and chlorinated aliphatic hydrocarbons, such as methylene chloride, as solvents.

Various methods for preparing aromatic carbonates have been previously described in the literature and/or utilized by industry. A method that has enjoyed substantial popularity in the literature involves the direct carbonylation of aromatic hydroxy compounds with carbon monoxide and oxygen. In general, practitioners have found that the carbonylation reaction requires a rather complex catalyst system. For example, in U.S. Pat. No. 4,187,242, which is assigned to the assignee of the present invention, Chalk reports that a carbonylation catalyst system should contain a Group VIII B metal, such as ruthenium, rhodium, palladium, osmium, iridium, platinum, or a complex thereof. Further refinements to the carbonylation reaction include the identification of organic co-catalysts, such as terpyridines, phenanthrolines, quinolines and isoquinolines in U.S. Pat. No. 5,284,964 and the use of certain halide compounds, such as quaternary ammonium or phosphonium halides in U.S. Pat. No. 5,399,734, both patents also being assigned to the assignee of the present invention.

The economics of the carbonylation process is strongly dependent on the number of moles of aromatic carbonate produced per mole of Group VIII B metal utilized (i.e. "catalyst turnover"). Consequently, much work has been directed to the identification of efficacious inorganic co-catalysts that increase catalyst turnover. In U.S. Pat. No. 5,231,210, which is also assigned to General Electric Company, Joyce et al. report the use of a cobalt pentadentate complex as an inorganic co-catalyst ("IOCC"). In U.S. Pat. No. 5,498,789, Takagi et al. report the use of lead as an IOCC. In U.S. Pat. No. 5,543,547, Iwane et al. report the use of trivalent cerium as an IOCC. In U.S. Pat. No. 5,726,340, Takagi et al. report the use of lead and cobalt as a binary IOCC system. In Japanese Unexamined Patent Application No. 10-316627, Yoneyama et al. report the use of manganese and the combination of manganese and lead as IOCC's.

The literature is silent, however, as to the role of the IOCC in the carbonylation reaction (i.e. the reaction mechanism). Accordingly, meaningful guidance regarding the identification of additional IOCC systems is cursory at best. Periodic table groupings have failed to provide guidance in identifying additional IOCC's. For example, U.S. Pat. No. 5,856,554 provides a general listing of possible IOCC candidates, yet further analysis has revealed that many of the members (and combinations of members) of the recited groups (i.e., Groups IV B and V B) do not catalyze the carbonylation reaction. Therefore, due to the lack of guidance in the literature, the identification of effective carbonylation catalyst systems has become a serendipitous exercise.

As the demand for high performance plastics has continued to grow, new and improved methods of providing product more economically are needed to supply the market. In this context, various processes and catalyst systems are constantly being evaluated; however, the identities of improved and/or additional effective catalyst systems for these processes continue to elude the industry. Consequently, a long felt, yet unsatisfied need exists for new and improved methods and catalyst systems for producing aromatic carbonates and the like.

SUMMARY OF THE INVENTION

Accordingly, the present invention is directed to a catalyst system for producing aromatic carbonates. In one embodiment, the present invention provides a carbonylation catalyst system that includes a catalytic amount of an inorganic co-catalyst containing bismuth.

In various alternative embodiments, the carbonylation catalyst system can include an effective amount of a palladium source and an effective amount of a halide composition. Further alternative embodiments can include catalytic amounts of various co-catalyst combinations, such as bismuth and copper; bismuth, copper, and titanium; bismuth, copper and iron; bismuth and cerium; bismuth and manganese; bismuth, manganese, and europium; bismuth, manganese, and iron; bismuth, manganese and cerium; bismuth and europium; bismuth and nickel; bismuth and zinc; bismuth and iron; bismuth and cobalt; bismuth and iridium; bismuth and ruthenium; bismuth and rhodium; and bismuth and zirconium.

BRIEF DESCRIPTION OF THE DRAWING

Various features, aspects, and advantages of the present invention will become more apparent with reference to the following description, appended claims, and accompanying drawing, wherein the FIGURE is a schematic view of a device capable of performing an aspect of an embodiment of the present invention.

DETAILED DESCRIPTION

The present invention is directed to a catalyst system for producing aromatic carbonates. In one embodiment, the carbonylation catalyst system includes a catalytic amount of an inorganic co-catalyst containing bismuth. In alternative embodiments, the catalyst system can include an effective amount of a Group VIII B metal and an effective amount of a halide composition.

Unless otherwise noted, the term "effective amount," as used herein, includes that amount of a substance capable of either increasing (directly or indirectly) the yield of the carbonylation product or increasing selectivity toward an aromatic carbonate. Optimum amounts of a given reactant can vary based on reaction conditions and the identity of other constituents yet can be readily determined in light of the discrete circumstances of a given application.

Aromatic hydroxy compounds which may be used in the practice of the present invention include aromatic mono or polyhydroxy compounds, such as phenol, cresol, xylenol, resorcinol, hydroquinone, and bisphenol A. Aromatic organic mono hydroxy compounds are preferred, with phenol being more preferred.

In various preferred embodiments, the carbonylation catalyst system can contain at least one constituent from the Group VIII B metals or a compound thereof. A preferred Group VIII B constituent is an effective amount of a palladium source. In various embodiments, the palladium source may be in elemental form, or it may be employed as a palladium compound. Accordingly, palladium black or elemental palladium deposited on carbon may be used as well as palladium halides, nitrates, carboxylates, oxides and palladium complexes containing carbon monoxide, amines, phosphines or olefins. As used herein, the term "complexes" includes coordination or complex compounds containing a central ion or atom. The complexes may be nonionic, cationic, or anionic, depending on the charges carried by the central atom and the coordinated groups. Other common names for these complexes include complex ions (if electrically charged), Werner complexes, and coordination complexes.

In various applications, it may be preferable to utilize palladium (II) salts of organic acids, including carboxylates with $C_{2-6}$ aliphatic acids. Palladium(II) acetylacetonate is also a suitable palladium source. Preferably, the amount of Group VIII B metal source employed should be sufficient to provide about 1 mole of metal per 800–10,000 moles of aromatic hydroxy compound. More preferably, the proportion of Group VIII B metal source employed should be sufficient to provide about 1 mole of metal per 2,000–5,000 moles of aromatic hydroxy compound.

The carbonylation catalyst system may further contain an effective amount of a halide composition, such as an organic halide salt. In various preferred embodiments, the halide composition can be an organic bromide salt. The salt may be a quaternary ammonium or phosphonium salt, or a hexaalkylguanidinium bromide. In various embodiments, α, ω-bis(pentaalkylguanidinium)alkane salts may be preferred. Suitable organic halide compositions include tetrabutylammonium bromide, tetraethylammonium bromide, and hexaethylguanidinium bromide. In preferred embodiments, the carbonylation catalyst system can contain between about 5 and about 1000 moles of bromide per mole of palladium employed, and, more preferably, between about 50 and about 150 molar equivalents of bromide are used.

The formation of diaryl carbonates in a carbonylation reaction can be accompanied by the formation of by-products, such as bisphenols, in varying proportions. In order to increase selectivity to diaryl carbonate, various organic co-catalysts may be incorporated in the carbonylation catalyst system. Depending on the application, suitable organic co-catalyst may include various phosphine, quinone, terpyridine, phenanthroline, quinoline and isoquinoline compounds and their derivatives, such as 2,2':6',2-terpyridine, 4'-methylthio-9,2':6',2-terpyridine, 2,2':6',2-terpyridine N-oxide, 1,10-phenanthroline, 9,4,7,8-tetramethyl-1,10-phenanthroline, 4,7-diphenyl-1,10-phenanthroline and 3,4,7,8-tetramethyl-1,10-phenanthroline.

The carbonylation catalyst system includes a catalytic amount of an inorganic co-catalyst (IOCC) containing bismuth. In addition to bismuth per se, it has been discovered that certain IOCC combinations can effectively catalyze the carbonylation reaction. Such IOCC combinations include bismuth and copper; bismuth, copper, and titanium; bismuth, copper and iron; bismuth and cerium; bismuth and manganese; bismuth, manganese, and europium; bismuth, manganese, and iron; bismuth, manganese and cerium; bismuth and europium; bismuth and nickel; bismuth and zinc; bismuth and iron; bismuth and cobalt; bismuth and iridium; bismuth and ruthenium; bismuth and rhodium; and bismuth and zirconium.

An IOCC can be introduced to the carbonylation reaction in various forms, including salts and complexes, such as tetradentate, pentadentate, hexadentate, or octadentate complexes. Illustrative forms may include oxides, halides, carboxylates, diketones (including beta-diketones), nitrates, complexes containing carbon monoxide or olefins, and the like. Suitable beta-diketones include those known in the art as ligands for the IOCC metals of the present invention. Examples include, but are not limited to, acetylacetone, benzoylacetone, dibenzoylmethane, diisobutyrylmethane, 2,2-dimethylheptane-3,5-dione, 2,2,6-trimethylheptane-3,5-dione, dipivaloylmethane, and tetramethylheptanedione. The quantity of ligand is preferably not such that it interferes with the carbonylation reaction itself, with the isolation or purification of the product mixture, or with the recovery and reuse of catalyst components (such as palladium). An IOCC may be used in its elemental form if sufficient reactive surface area can be provided. In embodiments employing supported palladium, it is noted that the bismuth-based IOCC provides a discrete, catalytic source of bismuth in a form favorable for such catalysis.

IOCC's are included in the carbonylation catalyst system in catalytic amounts. In this context a "catalytic amount" is an amount of IOCC (or combination of IOCC's) that increases the number of moles of aromatic carbonate produced per mole of Group VIII B metal utilized; increases the number of moles of aromatic carbonate produced per mole of halide utilized; or increases selectivity toward aromatic carbonate production beyond that obtained in the absence of the IOCC (or combination of IOCC's). Optimum amounts of an IOCC in a given application will depend on various factors, such as the identity of reactants and reaction conditions. For example, when palladium is included in the reaction, the molar ratio of bismuth relative to palladium at the initiation of the reaction is preferably between about 0.1 and about 100. Additional IOCC's may be used in the carbonylation catalyst system, provided the additional IOCC does not deactivate (i.e. "poison") the original IOCC.

The carbonylation reaction can be carried out in a batch reactor or a continuous reactor system. Due in part to the low solubility of carbon monoxide in organic hydroxy compounds, such as phenol, it is preferable that the reactor vessel be pressurized. In preferred embodiments, gas can be supplied to the reactor vessel in proportions of between about 2 and about 50 mole percent oxygen, with the balance being carbon monoxide. Additional gases may be present in amounts that do not deleteriously affect the carbonylation reaction. The gases may be introduced separately or as a mixture. A total pressure in the range of between about 10 and about 250 atmospheres is preferred. Drying agents, typically molecular sieves, may be present in the reaction vessel. Reaction temperatures in the range of between about 60° C. and about 150° C. are preferred. Gas sparging or mixing can be used to aid the reaction.

In order that those skilled in the art will be better able to practice the present invention reference is made to the FIGURE, which shows an example of a continuous reactor system for producing aromatic carbonates. The symbol "V" indicates a valve and the symbol "P" indicates a pressure gauge.

The system includes a carbon monoxide gas inlet 10, an oxygen inlet 11, a manifold vent 12, and an inlet 13 for a gas, such as carbon dioxide. A reaction mixture can be fed into a low pressure reservoir 20, or a high pressure reservoir 21, which can be operated at a higher pressure than the reactor for the duration of the reaction. The system further includes a reservoir outlet 22 and a reservoir inlet 23. The gas feed pressure can be adjusted to a value greater than the desired reactor pressure with a pressure regulator 30. The gas can be purified in a scrubber 31 and then fed into a mass flow controller 32 to regulate flow rates. The reactor feed gas can be heated in a heat exchanger 33 having appropriate conduit prior to being introduced to a reaction vessel 40. The reaction vessel pressure can be controlled by a back pressure regulator 41. After passing through a condenser 25, the reactor gas effluent may be either sampled for further analysis at valve 42 or vented to the atmosphere at valve 50. The reactor liquid can be sampled at valve 43. An additional valve 44 can provide further system control, but is typically closed during the gas flow reaction.

In the practice of one embodiment of the invention, the carbonylation catalyst system and aromatic hydroxy compound are charged to the reactor system. The system is sealed. Carbon monoxide and oxygen are introduced into an appropriate reservoir until a preferred pressure (as previously defined) is achieved. Circulation of condenser water is initiated, and the temperature of the heat exchanger 33 (e.g., oil bath) can be raised to a desired operating temperature. A conduit 46 between heat exchanger 33 and reaction vessel 40 can be heated to maintain the desired operating temperature. The pressure in reaction vessel 40 can be controlled by the combination of reducing pressure regulator 30 and back pressure regulator 41. Upon reaching the desired reactor temperature, aliquots can be taken to monitor the reaction.

EXAMPLES

The following examples are included to provide additional guidance to those skilled in the art in practicing the claimed invention. While some of the examples are illustrative of various embodiments of the claimed invention, others are comparative and are identified as such. The examples provided are merely representative of the work that contributes to the teaching of the present application. Accordingly, these examples are not intended to limit the invention as defined in the appended claims, in any manner. Unless otherwise specified, all parts are by weight, and all equivalents are relative to palladium. Reaction products were verified by gas chromatography. All reactions were carried out in a glass batch reactor at 90–100° C. in a 10% $O_2$ in CO atmosphere at an operating pressure of 95–102 atm. Reaction time was generally 2–3 hours.

As discussed supra, the economics of aromatic carbonate production is dependent on the number of moles of aromatic carbonate produced per mole of Group VIII B metal utilized. In the following examples, the aromatic carbonate produced is diphenylcarbonate (DPC) and the Group VIII B metal utilized is palladium. For convenience, the number of moles of DPC produced utilized is palladium utilized is referred to as the palladium turnover number (Pd TON).

Baseline Example

In order to determine the comparative efficacy of various embodiments of the present invention, baseline data were produced by adding, at ambient conditions, 0.25 mM palladium(II) acetylacetonate and various amounts of halide compositions to a glass reaction vessel containing phenol. The reactants were heated to 100° C. for 3 hours in a 10% oxygen in carbon monoxide atmosphere. After the reaction, samples were analyzed for DPC by gas chromatography producing the following results:

| Experiment No. | Pd ppm | HegBr Equivalents | Pd TON |
|---|---|---|---|
| 1 | 25 | 0 | 82.3 |
| 2 | 25 | 30 | 75.5 |
| 3 | 25 | 60 | 50.3 |
| 4 | 25 | 120 | 46.3 |
| 5 | 25 | 240 | 44.2 |
| 6 | 25 | 600 | 38.7 |

Example 1

Diphenyl carbonate was produced by adding, at ambient conditions, palladium(II) acetylacetonate, hexaethylguanidinium bromide ("HegBr"), and bismuth(II) tetramethylheptanedionate as an inorganic co-catalyst to a glass reaction vessel containing phenol. The reactants were heated to 100° C. for 3 hours in a 10% oxygen in carbon monoxide atmosphere. After the reaction, samples were analyzed for DPC by gas chromatography. The following results were observed:

| Experiment No. | Pd Ppm | Bi Equivalents | Br Equivalents | Pd TON |
|---|---|---|---|---|
| 1 | 25 | 14 | 30 | 230 |
| 2 | 25 | 14 | 60 | 266 |
| 3 | 25 | 14 | 120 | 285 |
| 4 | 25 | 28 | 30 | 243 |
| 5 | 25 | 28 | 120 | 368 |

The various reaction condition show that a Pd TON at least as high as 368 can be obtained utilizing bismuth as an IOCC. Based on the results of these experiments, it is evident that an IOCC containing bismuth can effectively catalyze the carbonylation reaction.

Example 2

The general procedure of Example 1 was repeated with 25 ppm palladium(II) acetylacetonate, 60 equivalents of bromide in the form of hexaethylguanidinium bromide, and the following IOCC combination: 14 equivalents of bismuth in the form of bismuth(II)tetramethylheptanedionate and 14 equivalents of copper in the form of copper(II) acetylacetonate. The Pd TON was found to be 381, thus showing that the IOCC combination of bismuth and copper can effectively catalyze the carbonylation reaction.

Example 3

The general procedure of Examples 1 and 2 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate, 14 equivalents of copper in the form of copper(II) acetylacetonate, and 14 equivalents of titanium in the form of titanium(IV) oxide acetylacetonate. The Pd TON was found to be 426, thus showing that the IOCC combination of bismuth, copper, and titanium can effectively catalyze the carbonylation reaction.

Example 4

The general procedure of Examples 1–3 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate, 14 equivalents of copper in the form of copper(II) acetylacetonate, and 14 equivalents of iron in the form of iron(III) acetylacetonate. The Pd TON was found to be 929, thus showing that the IOCC combination of bismuth, copper, and iron can effectively catalyze the carbonylation reaction.

Example 5

The general procedure of Examples 1–4 was repeated with 25 ppm palladium(I) acetylacetonate, 60 equivalents of bromide in the form of hexaethylguanidinium bromide, and the following IOCC combination: 14 equivalents of bismuth in the form of bismuth(II)tetramethylheptanedionate and 14 equivalents of cerium in the form of cenium(III) acetylacetonate. The Pd TON was found to be 734, thus showing that the IOCC combination of bismuth and cerium can effectively catalyze the carbonylation reaction.

Example 6

The general procedure of Examples 1–5 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate and 14 equivalents of manganese in the form of manganese(III) acetylacetonate. The Pd TON was found to be 709, thus showing that the IOCC combination of bismuth and manganese can effectively catalyze the carbonylation reaction.

The reaction was repeated with 25 ppm palladium(II) acetylacetonate and various amounts of bromide and IOCC to provide the following results:

| Experiment No. | Mn(acac)$_3$ Equivalents | Bi(TMHD)$_2$ Equivalents | HegBr Equivalents | Pd TON |
|---|---|---|---|---|
| 1 | 14 | 2.8 | 120 | 645 |
| 2 | 14 | 2.8 | 30 | 583 |
| 3 | 28 | 5.6 | 120 | 728 |
| 4 | 28 | 5.6 | 30 | 564 |
| 5 | 2.8 | 14 | 120 | 818 |
| 6 | 2.8 | 14 | 30 | 477 |
| 7 | 5.6 | 28 | 120 | 1075 |
| 8 | 5.6 | 28 | 30 | 556 |

Based on the results of these experiments, it is evident that the combination of higher bismuth content, lower manganese content, and higher bromide content may provide superior performance under certain reaction conditions.

Example 7

The general procedure of Examples 1–6 was repeated with 25 ppm palladium(II) acetylacetonate and the following IOCC combination: 14 equivalents of bismuth in the form of bismuth(II)tetramethylheptanedionate, 14 equivalents of manganese in the form of manganese(III) acetylacetonate, and 14 equivalents of europium in the form of europium(III) acetylacetonate. No bromide was added. The Pd TON was found to be 198, thus showing that the IOCC combination of bismuth, manganese, and europium can effectively catalyze the carbonylation reaction even in the absence of bromide.

The reaction was repeated with 25 ppm palladium(II) acetylacetonate and various amounts of bromide and IOCC to provide the following results:

| Exp. No. | Mn(acac)$_3$ Equivalents | Bi(TMHD)$_2$ Equivalents | Eu(acac)$_3$ Equivalents | HegBr Equivalents | Pd TON |
|---|---|---|---|---|---|
| 1 | 14 | 4 | 4 | 120 | 806 |
| 2 | 14 | 4 | 4 | 240 | 600 |
| 3 | 14 | 4 | 14 | 120 | 1066 |
| 4 | 14 | 4 | 14 | 240 | 954 |
| 5 | 14 | 4 | 56 | 120 | 757 |
| 6 | 14 | 4 | 56 | 240 | 603 |
| 7 | 14 | 14 | 4 | 120 | 920 |
| 8 | 14 | 14 | 4 | 240 | 833 |
| 9 | 14 | 14 | 14 | 120 | 1126 |
| 10 | 14 | 14 | 14 | 240 | 1098 |
| 11 | 14 | 14 | 56 | 120 | 1339 |
| 12 | 14 | 14 | 56 | 240 | 1289 |
| 13 | 14 | 56 | 4 | 120 | 864 |
| 14 | 14 | 56 | 4 | 240 | 1150 |
| 15 | 14 | 56 | 14 | 120 | 1275 |
| 16 | 14 | 56 | 14 | 240 | 1408 |
| 17 | 14 | 56 | 56 | 120 | 1681 |
| 18 | 14 | 56 | 56 | 240 | 2071 |
| 19 | 28 | 4 | 4 | 120 | 769 |
| 20 | 28 | 4 | 4 | 240 | 626 |
| 21 | 28 | 4 | 14 | 120 | 569 |
| 22 | 28 | 4 | 14 | 240 | 424 |
| 23 | 28 | 4 | 56 | 120 | 333 |
| 24 | 28 | 4 | 56 | 240 | 244 |
| 25 | 28 | 14 | 4 | 120 | 905 |
| 26 | 28 | 14 | 4 | 240 | 772 |
| 27 | 28 | 14 | 14 | 120 | 890 |
| 28 | 28 | 14 | 14 | 240 | 975 |
| 29 | 28 | 14 | 56 | 120 | 711 |
| 30 | 28 | 14 | 56 | 240 | 545 |
| 31 | 28 | 56 | 4 | 120 | 720 |
| 32 | 28 | 56 | 4 | 240 | 967 |
| 33 | 28 | 56 | 14 | 120 | 952 |
| 34 | 28 | 56 | 14 | 240 | 1359 |
| 35 | 28 | 56 | 56 | 120 | 1356 |
| 36 | 28 | 56 | 56 | 240 | 1524 |

The various reaction conditions show that a Pd TON at least as high as 2071 can be obtained utilizing the IOCC combination of bismuth, manganese, and europium.

Example 8

The general procedure of Examples 1–7 was repeated with 25 ppm palladium(II)acetylacetonate, 60 equivalents of bromide in the form of hexaethylguanidinium bromide, and the following IOCC combination: 14 equivalents of bismuth in the form of bismuth(II)tetramethylheptanedionate, 14 equivalents of manganese in the form of manganese(III) acetylacetonate, and 14 equivalents of iron in the form of iron(III) acetylacetonate. The Pd TON was found to be 1003, thus showing that the IOCC combination of bismuth, manganese, and iron can effectively catalyze the carbonylation reaction.

Example 9

The general procedure of Examples 1–8 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate and 14 equivalents of europium in the form of europium(III) acetylacetonate. The Pd TON was found to be 376, thus showing that the IOCC combination of bismuth and europium can effectively catalyze the carbonylation reaction.

Example 10

The general procedure of Examples 1–9 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate and 14 equivalents of nickel in the form of nickel(II) acetylacetonate. The Pd TON was found to be 265, thus showing that the IOCC combination of bismuth and nickel can effectively catalyze the carbonylation reaction.

Example 11

The general procedure of Examples 1–10 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate, 14 equivalents of manganese in the form of manganese(III) acetylacetonate, and 14 equivalents of cerium in the form of cerium(III) acetylacetonate. The Pd TON was found to be 817, thus showing that the IOCC combination of bismuth, manganese, and cerium can effectively catalyze the carbonylation reaction.

Example 12

The general procedure of Examples 1–11 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate and 14 equivalents of zinc in the form of zinc((II) acetylacetonate. The Pd TON was found to be 357, thus showing that the IOCC combination of bismuth and zinc can effectively catalyze the carbonylation reaction.

Example 13

The general procedure of Examples 1–12 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate and 14 equivalents of iron in the form of iron(III) acetylacetonate. The Pd TON was found to be 578, thus showing that the IOCC combination of bismuth and iron can effectively catalyze the carbonylation reaction. The reaction was repeated with 25 ppm palladium(II) acetylacetonate and various amounts of bromide and IOCC to provide the following results:

| Experiment No. | Fe(acac)$_3$ Equivalents | Bi(TMHD)$_2$ Equivalents | HegBr Equivalents | Pd TON |
| --- | --- | --- | --- | --- |
| 1 | 2.8 | 14 | 120 | 372 |
| 2 | 2.8 | 14 | 30 | 216 |
| 3 | 5.6 | 28 | 120 | 368 |
| 4 | 5.6 | 28 | 30 | 231 |
| 5 | 14 | 2.8 | 120 | 208 |
| 6 | 14 | 2.8 | 30 | 474 |
| 7 | 28 | 5.6 | 120 | 377 |
| 8 | 28 | 5.6 | 30 | 732 |

Based on the results of these experiments, it is evident that the combination of lower bismuth content, higher iron content, and lower bromide content may provide superior performance under certain reaction conditions.

Example 14

The general procedure of Examples 1–13 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate and 14 equivalents of cobalt in the form of cobalt(IT) acetylacetonate. The Pd TON was found to be 122, thus showing that the IOCC combination of bismuth and cobalt can effectively catalyze the carbonylation reaction.

Example 15

The general procedure of Examples 1–14 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate and 14 equivalents of iridium in the form of iridium(III) acetylacetonate. The Pd TON was found to be 267, thus showing that the IOCC combination of bismuth and iridium can effectively catalyze the carbonylation reaction.

Example 16

The general procedure of Examples 1–15 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate and 14 equivalents of ruthenium in the form of ruthenium(III) acetylacetonate. The Pd TON was found to be 200, thus showing that the IOCC combination of bismuth and ruthenium can effectively catalyze the carbonylation reaction.

Example 17

The general procedure of Examples 1–16 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate and 14 equivalents of rhodium in the form of rhodium(III) acetylacetonate. The Pd TON was found to be 212, thus showing that the IOCC combination of bismuth and rhodium can effectively catalyze the carbonylation reaction.

Example 18

The general procedure of Examples 1–17 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate and 14 equivalents of zirconium in the form of zirconium(IV) acetylacetonate. The Pd TON was found to be 404, thus showing that the IOCC combination of bismuth and zirconium can effectively catalyze the carbonylation reaction.

Comparative Example A

It has been determined that several potential IOCC candidates do not catalyze the carbonylation reaction and in fact may poison an otherwise effective IOCC combination. For example, the general procedure of Examples 1–18 was repeated with 25 ppm palladium(II) acetylacetonate, 60 equivalents of bromide in the form of hexaethylguanidinium bromide, and 14 equivalents of antimony in the form of antimony(III)bromide as a potential IOCC candidate. The Pd TON was found to be zero, thereby showing that Sb(III) does not effectively catalyze the carbonylation reaction at the conditions used.

Comparative Example B

The general procedure of Examples 1–18 was repeated with 25 ppm palladium(II) acetylacetonate, 60 equivalents of bromide in the form of hexaethylguanidinium bromide, and the following IOCC combination: 14 equivalents of bismuth in the form of bismuth(II) tetramethylheptanedionate and 14 equivalents of antimony in the form of $SbBr_3$. The Pd TON was found to be zero, thereby showing that, in addition to failing to effectively catalyze the carbonylation reaction as a sole IOCC, Sb(III) can poison an otherwise effective IOCC (i.e. bismuth) at the conditions used.

Comparative Example C

The general procedure of Examples 1–18 was repeated with 25 ppm palladium(II) acetylacetonate, 60 equivalents of bromide in the form of hexaethylguanidinium bromide, and 14 equivalents of vanadium in the form of vanadium(III) acetylacetonate as a potential IOCC candidate. The Pd TON was found to be zero, thereby showing that V(III) does not effectively catalyze the carbonylation reaction at the conditions used.

Comparative Example D

The general procedure of Examples 1–18 was repeated with 25 ppm palladium(II) acetylacetonate, 60 equivalents of bromide in the form of hexaethylguanidinium bromide, and 14 equivalents of vanadium in the form of vanadium (IV) oxide acetylacetonate as a potential IOCC candidate. The Pd TON was found to be zero, thereby showing that V(IV) does not effectively catalyze the carbonylation reaction at the conditions used.

It will be understood that each of the elements described above, or two or more together, may also find utility in applications differing from the types described herein. While the invention has been illustrated and described as embodied in a method and catalyst system for producing aromatic carbonates, it is not intended to be limited to the details shown, since various modifications and substitutions can be made without departing in any way from the spirit of the present invention. For example, additional effective IOCC compounds can be added to the reaction. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A carbonylation catalyst system, comprising an effective amount of a palladium source and catalytic amounts of an inorganic co-catalyst comprising bismuth, said effective and catalytic amounts being amounts capable of increasing the yield of aromatic carbonate in the reaction of an aromatic hydroxy compound, carbon monoxide and oxygen or increasing selectivity of said reaction toward aromatic carbonate.

2. The carbonylation catalyst system of claim 1, comprising a catalytic amount of a combination of inorganic co-catalysts comprising bismuth and copper.

3. The carbonylation catalyst system of claim 2, wherein the combination of inorganic co-catalysts further comprises titanium.

4. The carbonylation catalyst system of claim 2, wherein the combination of inorganic co-catalysts further comprises iron.

5. The carbonylation catalyst system of claim 1, comprising a catalytic amount of a combination of inorganic co-catalysts comprising bismuth and cerium.

6. The carbonylation catalyst system of claim 1, comprising a catalytic amount of a combination of inorganic co-catalysts comprising bismuth and manganese.

7. The carbonylation catalyst system of claim 6, wherein the combination of inorganic co-catalysts further comprises europium.

8. The carbonylation catalyst system of claim 6, wherein the combination of inorganic co-catalysts further comprises iron.

9. The carbonylation catalyst system of claim 6, wherein the combination of inorganic co-catalysts further comprises cerium.

10. The carbonylation catalyst system of claim 1, comprising a catalytic amount of a combination of inorganic co-catalysts comprising bismuth and europium.

11. The carbonylation catalyst system of claim 1, comprising a catalytic amount of a combination of inorganic co-catalysts comprising bismuth and nickel.

12. The carbonylation catalyst system of claim 1, comprising a catalytic amount of a combination of inorganic co-catalysts comprising bismuth and zirconium.

13. The carbonylation catalyst system of claim 1, comprising a catalytic amount of a combination of inorganic co-catalysts comprising bismuth and zinc.

14. The carbonylation catalyst system of claim 1, comprising a catalytic amount of a combination of inorganic co-catalysts comprising bismuth and iron.

15. The carbonylation catalyst system of claim 1, comprising a catalytic amount of a combination of inorganic co-catalysts comprising bismuth and cobalt.

16. The carbonylation catalyst system of claim 1, comprising a catalytic amount of a combination of inorganic co-catalysts comprising bismuth and iridium.

17. The carbonylation catalyst system of claim 1, comprising a catalytic amount of a combination of inorganic co-catalysts comprising bismuth and ruthenium.

18. The carbonylation catalyst system of claim 1, comprising a catalytic amount of a combination of inorganic co-catalysts comprising bismuth and rhodium.

19. The carbonylation catalyst system of claim 1, comprising a catalytic amount of a combination of inorganic co-catalysts comprising bismuth and a substance selected from the group consisting of copper; copper and titanium; copper and iron; cerium; manganese; manganese and europium; manganese and iron; manganese and cerium; europium; nickel; zinc; iron; cobalt; iridium; ruthenium; rhodium; and zirconium.

20. The carbonylation catalyst system of claim 1, wherein the palladium source is a Pd(II) salt or complex.

21. The carbonylation catalyst system of claim 20, wherein the palladium source is palladium acetylacetonate.

22. The carbonylation catalyst system of claim 1, wherein the palladium source is supported Pd.

23. The carbonylation catalyst system of claim 22, wherein the palladium source is palladium on carbon.

24. The carbonylation catalyst system of claim 1, further comprising an a halide composition.

25. The carbonylation catalyst system of claim 24, wherein the halide composition is tetraethylammonium bromide.

26. The carbonylation catalyst system of claim 24, wherein the halide composition is hexaethylguanidinium bromide.

27. The carbonylation catalyst system of claim 1, wherein the molar ratio of bismuth relative to palladium is between about 0.1 and about 100.

* * * * *